United States Patent [19]
Lowicki et al.

[11] 4,376,789
[45] Mar. 15, 1983

[54] SURFACTANTS WHICH ARE POLYHYDRIC ALCOHOL PARTIAL ESTERS OF ADDUCTS OF MALEIC ANHYDRIDE WITH AN UNSATURATED CARBOXYLIC ACID

[75] Inventors: Norbert Lowicki, Duisburg; Natvarlal B. Desai, Dinslaken, both of Fed. Rep. of Germany

[73] Assignee: Grillo-Werke AG, Duisburg-Hamborn, Fed. Rep. of Germany

[21] Appl. No.: 240,606

[22] Filed: Mar. 4, 1981

[30] Foreign Application Priority Data

Aug. 29, 1980 [DE] Fed. Rep. of Germany ....... 3032612

[51] Int. Cl.$^3$ ................... A61K 47/00; A61K 31/70; C07H 13/06; C07C 69/74
[52] U.S. Cl. ................... 424/361; 424/180; 424/314; 424/365; 536/119; 560/123; 562/505; 252/174.18; 549/245
[58] Field of Search ................ 260/346.6; 536/119; 424/180, 314, 361; 562/505; 560/123; 252/108, 121, 142, 174.18

[56] References Cited

U.S. PATENT DOCUMENTS 2,137,616 11/1938 Hunn ........................... 260/346.6
2,839,550 6/1958 Wiggerink et al. ............ 260/346.6
3,053,830 9/1962 Gaertner ....................... 536/119
3,219,657 11/1965 Gaertner ....................... 536/119
4,150,041 4/1979 Suzuki et al. ................. 260/346.6

OTHER PUBLICATIONS

Sastry et al.-J. Amer. Oil Chem. Soc., vol. 48 (1971), pp. 686-688.
Rheineck et al.-Fette-Seifen-Anstrichmit., vol. 71 (1969), pp. 644-652.
Nagakura-Chem. Abst., vol. 91 (1979), p. 22764h.
Vainer et al.-Chem. Abst., vol. 76 (1972), p. 29524d.
Nagakura et al.-Chem. Abst., vol. 83 (1975), p. 27496s.
Dow-Chem. Abst., vol. 83 (1975), p. 178328q.
Bibby-Chem. Abst., vol. 88 (1978), p. 22149z.
Suzuki-Chem. Abst., vol. 89 (1978), p. 76632r.
Asao et al.-Chem. Abst., vol. 84 (1976), p. 91,967u.
Broniarz et al.-Chem. Abst., vol. 79 (1973), p. 7158x.

Primary Examiner—Sam Rosen
Attorney, Agent, or Firm—Merriam, Marshall & Bicknell

[57] ABSTRACT

Disclosed are novel polyhydric alcohol partial esters of polycarboxylic acids from Diels-Alder adducts of maleic anhydride and a straight chain unsaturated carboxylic acid having ten to twenty-five carbon atoms. The partial esters can be subsequently sulfated.

The polyhydric alcohol can be a mono- or disaccharide such as sucrose or mannose.

The partial esters are surfactants which are dermatologially acceptable and useful in personal products and skin-care products.

12 Claims, No Drawings

SURFACTANTS WHICH ARE POLYHYDRIC ALCOHOL PARTIAL ESTERS OF ADDUCTS OF MALEIC ANHYDRIDE WITH AN UNSATURATED CARBOXYLIC ACID

This invention is concerned with partial esters of polyhydric alcohols, especially of mono- and disaccharides, with the polycarboxylic acids which result from the Diels-Alder adducts of maleic anhydride with simple unsaturated carboxylic acids having a chain length of $C_{10}$ to $C_{25}$ and which, if desired, can be sulfated. Further, the invention is concerned with processes of producing these products, as well as with their use as dermatologically acceptable nonionic and/or anionic surfactants in cosmetic preparations.

The Diels-Alder adducts of maleic anhydride with simple unsaturated carboxylic acids are known. They can be saponified with alkali, and their esters and amides, especially their reaction products with triethanolamine, are useful as anticorrosives; cf. U.S. Pat. No. 3,985,504. The alkali salts have already been used to prevent formation of deposits from hot seawater; cf. Great Britain Pat. No. 1,551,894.

The chemical structure of the adducts is not fully explained, since statements in the two above-mentioned patents are contradictory. According to U.S. Pat. No. 3,985,504 an addition of carbon atoms takes place next to the double bond, with the double bond remaining preserved. According to Great Britain Pat. No. 1,551,894 cyclobutanedicarboxylic acids are obtained. In any case, through hydrolysis of the adducts, tri- and poly- carboxylic acids are obtained.

It has now been found that polyhydric alcohol partial esters, especially of mono- and disaccharides, with polycarboxylic acids which result from a Diels-Alder adduct of maleic anhydride with at least one unsaturated carboxylic acid having a chain length of $C_{10}$ to $C_{25}$, possess unusual and extremely valuable properties. The unsaturated carboxylic acid desirably has a straight carbon chain. It has been found that these partial esters are excellent dermatologically acceptable nonionic surfactants especially suitable for use in cosmetic preparations. Surprisingly, these partial esters can be sulfated under gentle conditions, with the double bond of the unsaturated carboxylic acids remaining unaltered as shown, for example, by the iodine number of the products. The sulfated partial esters likewise form extremely useful dermatologically acceptable anionic surfactants which are likewise especially suitable in cosmetic preparations.

The sulfated partial esters of mono- and disaccharides are the first sulfated sugar esters and they are especially useful in producing mild cleansers and dermatologically acceptable detergents.

The sulfation can be carried out in such mild conditions, namely at temperatures below 100° C., with sodium sulfite, that the process is not by any means comparable to the usual sulfation of olefins. It is believed, therefore, that in the sulfation of the products of the invention, a substitution takes place on an activated carbon atom of the maleic acid molecule. The partial esters of mono- and disaccharides, according to the invention, provide a completely new type of sugar ester and sugar-based surfactant, which by reason of their favorable toxicological and dermatological properties, are clearly superior to most, if not all, products hitherto known.

A specially advantageous property of the partial esters of the invention is their compatibility with hard water, with which they generate no precipitates.

Another surprising advantage is that the sugar esters of the invention are readily and easily produced on a large scale. According to *Industrial Engineering Chemistry*, 48 (1956), pages 1459 to 1464, sugar esters are produced, for example, by ester interchange of fatty acid alkyl esters with sugar in dimethyl formamide in the presence of an alkaline catalyst at about 90° C. The reaction time amounts to about 12 hours and purification of the reaction product is difficult, especially as to complete removal of the dimethyl formamide. A nearly quantitative recovery of this solvent is important for economic reasons. On the other hand, dimethyl formamide is not physiologically acceptable. Despite careful purification of the sugar ester obtained in this manner, for example a sucrose ester, small amounts of the physiologically objectionable dimethyl formamide remain in the end product and which, furthermore, cause a disagreeable odor.

According to German published patent application No. AS 20 22 880 the ester interchange of fatty acid esters with sucrose can occur through addition of 1 to 40% by weight of an alkali-free alkali salt or soap of saturated and unsaturated fatty acids, as a catalyst. The ester interchange is carried out at 160° to 190° C. within 20 minutes. After termination of the reaction, the remaining mixture is rapidly cooled and the unreacted sucrose, as well as the soap used as a catalyst, are removed. Although the process operates without solvents, the cost of preparing the alkali soap is very high. To prepare alkali-free soap, the alkali metal hydroxides are first dissolved in aqueous methanol under nitrogen by heating at a reflux temperature. Afterwards, the methyl ester of the selected long-chain fatty acid is added and the mixture is heated for 40 to 60 minutes under reflux. The methanol is then vacuum distilled from the soap formed in the process.

A further disadvantage of the described process is that yields of the sucrose ester amount to only about 43 to 48%. This is because it is difficult to control the high reaction temperatures so as to prevent disintegration of reactants, and the product, from occurring.

According to German published patent application No. AS 24 12 374, sucrose can be ester-interchanged with a triglyceride at 100° to 170° C. with use of alkaline catalysts. The yield of sucrose esters after 10 to 22 hours of reaction time is between 11 and 40%. Solid products are produced which are insoluble in water, or which are soluble only with great difficulty in water, and which react with the mineral content of the water.

The process according to German published patent application No. AS 24 12 374 cannot be applied to the production of unsaturated fatty acids since the long reaction times lead to formation of resinous products with insufficient dispersibility in oil. Finally, working-up of the sucrose esters produced in low yield is very expensive.

According to the invention, partial esters of polyhydric alcohols, particularly mono- and disaccharides, including partial esters of mannose, glucose and the very sensitive sucrose, can be produced at 85° to 90° C. within a reaction time of 1 to 5 hours by reaction with the adduct or a polycarboxylic acid formed by hydrolysis of the adduct. The partial ester products thus obtained are completely water soluble and provide, from the outset, excellent compatibility with the skin and mucous membranes. In the process of the invention, the reaction is carried out without solvents. In addition, about 5 to 10% by weight of an alkaline material, for example sodium hydroxide, potassium carbonate or trisodium phosphate, can be used as the catalyst. Surprisingly, as the reaction progresses, the viscosity of the reaction mixture decreases, while according to the prior art the reaction products became increasingly viscous and solid. The products of the invention are directly obtained as light-brown, low viscosity products that are very soluble in water and which can be used in cosmetic products without further purification. The reaction mixture contains at least 75% by weight of sugar ester, while according to the state of the art it was possible to obtain only sugar surfactants with a content of 30 to 45% sugar ester.

As already stated above, the partial esters produced according to the invention can be directly sulfonated with aqueous sodium sulfite. Viscous, very water soluble substances are produced in this way which, like the starting products, have pronounced surfactant and emulsifier properties. Moreover, these sulfonated partial esters are excellent solubilizers which aid in dissolving, for example, perfume oils, insoluble bactericides and other cosmetic adjuvants, in water and in water-alcohol mixtures.

Representative of the simple unsaturated carboxylic acids with a chain length of $C_{10}$ to $C_{25}$, preferably a chain length of $C_{10}$ to $C_{18}$, which can be used are ricinoleic acid, oleic acid, linoleic acid, palmitoleic acid, elaidic acid as well as undecylenic acid. Instead of the pure acids there can also be used fatty acid mixtures enriched with one or more of the above-mentioned unsaturated acids. Theoretically suitable are unsaturated fatty acids having an iodine number in the range of 35 to 140. Especially preferred acids are ricinoleic acid and undecylic acid. The use of undecylic acid as the unsaturated fatty acid component yields mildly bactericidal and fungicidal products. A special advantage of such products, compared to previously known undecylic acid derivatives, is that they are free of amino nitrogen and halogen and are, accordingly, physiologically unobjectionable.

Dihydric and other polyhydric alcohols suitable for use are, especially, ethylene glycol, glycerin, pentaerythrite as well as readily available sugars such as glucose, mannose, xylitol and sucrose. It is believed, however, that all polyhydric alcohols and their derivatives that are available in a sufficient amount and are physiologically unobjectionable can be used.

The process of the invention for the production of the partial esters, sulfonated if so desired, of a polyhydric alcohol with the Diels-Alder adducts of maleic anhydride with an unsaturated carboxylic acid takes place by direct reaction with the desired polyhydric alcohols. The Diels-Alder adduct can be used as such in the reaction or the adduct can be first hydrolyzed to a polycarboxylic acid. When the adduct is reacted directly with the polyhydric alcohol, the adduct anhydride ring structure opens to yield a polycarboxylic acid which then immediately reacts with the polyhydric alcohol. The resulting partial ester thus is a partial ester of a polycarboxylic acid, whether or not a hydrolysis of the adduct is first used. However, for the production of some partial esters, particularly partial esters of mono- and disaccharides, it is especially suitable to first hydrolyze the Diels-Alder adducts of maleic anhydride with the unsaturated carboxylic acids to form a polycarboxylic acid which then desirably is esterified with ethylene glycol. Thereafter, these partial esters can be subjected to ester interchange with the polyhydric alcohol. In this manner, especially pure and very compatible partial ester products are obtained which are produced under the most gentle conditions. They can be used directly in cosmetic products. If so desired, the partial ester is thereafter sulfonated with sodium sulfite at temperatures below 100° C. As already stated above, this sulfonation reaction is extremely surprising since, for example, esters of sucrose with ricinoleic acid do not react with sulfite. A determination of the iodine number of the sulfonated products of the invention shows that the iodine number has not changed and, accordingly, that the double bond in the unsaturated carboxylic acids obviously is preserved.

To perform the process of the invention, the fatty acid, or a fatty acid mixture, may be combined with maleic anhydride in a ratio of 1:1 to 1:2 and heated, without solvent and catalyst, to about 150° to 200° C. A reaction time of about 0.5 to 5 hours is suitable. The anhydride ring of the maleic anhydride adduct opens under gentle conditions, for example by water addition, resulting in polycarboxylic acids having an acid number range of from 200 to 350. When the polycarboxylic acids are heated with a temperature-stable polyhydric alcohol to 130° to 140° C., a condensation occurs, with splitting off of water, to form the partial esters of the invention. Depending on the degree of esterification, the partial esters have acid numbers of about 15 to 140. For the production of sugar esters, especially sucrose esters, ethylene glycol esters are preferably heated in a molar ratio of 1:1 to 1:0.5, to a temperature of 70° to 100° C., preferably 85° to 90° C. The ratio is selected based on the acid number of the partial esters so that at the end of the reaction none of the reactants will remain unreacted.

At low temperatures, the reaction proceeds relatively slowly. At temperatures above 100° C. the sucrose esters of the invention are darkly discolored.

When sulfonated partial esters are desired, sulfonation is carried out on the partial esters with aqueous sodium sulfite at temperatures between 70° and 80° C. In this process, in general, clear yellow viscous products are formed with high surfactant activity. The reaction conditions are so gentle, no inversion of the sucrose takes place.

The products of the invention can be used especially advantageously as dermatologically acceptable nonionic and/or anionic surfactants in cosmetic preparations. They can be used, for example, as surfactants in shampoos and as emulsifiers in cleansing cremes and lotions. Shampoos prepared according to the invention have the advantage of not degreasing the hair too severely nor denaturing the hair proteins. By reason of their solubilizing properties, they can be combined or mixed together very well with other substances conventionally used in cosmetics as, for example, vegetable oils, bactericides, deodorants and scents or perfumes which are difficultly soluble.

With the aid of surfactants of the invention formed by using undecylic acid as the starting material, hygienic agents can be produced having a gentle bactericidal and fungicidal action, which is especially desirable, for example, in personal products and food-care products. Such partial ester surfactants from undecylic acid act gently but significantly against bacteria and fungi which may appear, for example, in a person's intimate regions, and which also may spoil cosmetic preparations.

For the above reasons the products of the invention are especially useful in protecting or preserving the skin since no physiologically harmful effect is to be expected.

The following examples are presented to illustrate the invention in further detail. Quantities of materials are given as parts or percentages by weight unless otherwise indicated.

EXAMPLE 1

298.45 g of ricinoleic acid (1 mole) is reacted in a three-necked flask with 98 g (1 mole) of maleic anhydride without a solvent and without a catalyst, with agitation under a nitrogen atmosphere at 170°–175° C. for 5 hours. After termination of the reaction, the reaction product is cooled to 60°–70° C. and 18 g of water is added. The acid number of the resulting polycarboxylic acid is 255.

The polycarboxylic acid is then esterified in the same reaction vessel with 95 g of ethylene glycol at 130°–135° C. until 23.5 g of water is split-off or condenses. This reaction yields a partial ester having an acid number of 80.

The partial ester is reacted with 173.2 g of sucrose and 45.85 g of potassium carbonate at 85°–90° C. with agitation under a nitrogen stream for 5 hours to form 523 g of a light-brown, viscous product. The crude ester is absorbed in 700 ml of n-butanol and washed three times with 250 ml of 7% aqueous sodium chloride solution and the oily residue is absorbed in chloroform. The chloroform extract is filtered off and the chloroform separated in a rotary evaporator from the 354.3 g of sucrose partial ester (67.7% yield with respect to the total reaction product) which is obtained as a light-brown liquid.

The ester interchange with monosaccharides, for example glucose or mannose, takes place in an analogous manner.

Characterizing data of the sucrose ester:
Surface tension: 38.1 dyn·cm$^{-1}$
Saponification number: 287
pH (1% solution): 8.1

EXAMPLE 2

1 kg of a sucrose partial ester is prepared from ricinoleic acid, maleic anhydride and sucrose according to Example 1.

The partial ester is sulfonated in a three-necked flask provided with agitator and reflux cooler, with 272 g of sodium sulfite heptahydrate dissolved in 272 g of water, at 70° C. in 5 hours.

After termination of the reaction, there is obtained 1530 g of a clear yellow viscous product with very good solubility in tap water.

EXAMPLE 3

298.45 g of ricinoleic acid (1 mole) is reacted with 98 g of maleic anhydride (1 mole) according to Example 1 and esterified with ethylene glycol to such an extent that there arises a partial ester with the acid number of 30 to 40.

523 g of the partial ester is reacted with 177.8 g of sucrose and 75 g of sodium methylate solution (25%) at 85° C. with agitation under a nitrogen stream for 5 hours.

The reaction mixture is thereafter freed of methanol in a rotary evaporator and 698 g of a light-brown crude sucrose partial ester is obtained. Purification of the crude sugar ester according to Example 1 yields 467.7 g (67% with respect to the total reaction product) of sucrose partial ester.

Characterizing data of the sucrose partial ester:
Surface tension: 39.3 dyn·cm$^{-1}$
Saponification number: 295
pH (1% solution): 8.0

EXAMPLE 4

298.45 g of ricinoleic acid (1 mole) is reacted with 98 g of maleic anhydride (1 mole) according to Example 1 and esterified with ethylene glycol. The resulting product is a partial ester with an acid number of about 10.

400 g of the partial ester is reacted with 80 g of sucrose and 10 g of potassium carbonate according to Example 1. After 5 hours of reaction time there is obtained 467 g of a light-brown highly viscous product with the following characterizing data.

Characterizing data of the sucrose partial ester:
Surface tension: 40.3 dyn·cm$^{-1}$
Saponification number: 283
pH (1% solution): 8.4

EXAMPLE 5

184.3 g of undecylenic acid (1 mole) is reacted with 98 g of maleic anhydride (1 mole) according to Example 1 and esterified with ethylene glycol. This yields a partial ester with an acid number of about 100.

The partial ester is sulfated with 252 g of sodium sulfite heptahydrate dissolved in 300 g of water at 80° C. in one hour to yield a clear, light-brown strongly foaming solution with bactericidal and fungicidal activity. The surface tension of this product is 29.3 dyn·cm$^{-1}$.

EXAMPLE 6

184.3 g of undecylenic acid (1 mole) is reacted with 98 g of maleic anhydride (1 mole) according to Example 1 and esterified with 184.14 g of glycerin (2 moles) to yield 454 g of a light-yellow highly viscous partial ester with very good emulsifying, as well as bactericidal and fungicidal, acitivity.

The following Examples 7 to 16 illustrate use of the above-described surfactants for the production of cosmetic preparations.

EXAMPLE 7

| Face-cleansing Creme | |
|---|---|
| Compound according to Example 3 | 10.0 |
| Cremophor A 25 | 2.0 |
| (Ethoxylated fatty alcohol - BASF) | |
| Cetyl alcohol | 7.0 |
| Miglyol 812 | 5.0 |
| (Triglyceride of saturated vegetable fatty acids) | |
| Preservative | 0.2 |
| (Methyl-4-hydroxybenzoate Na salt) | |
| H$_2$O | 68.8 |
| | 100.0 |

EXAMPLE 8

| Day Creme | |
|---|---|
| Compound according to Example 1 | 8.0 |
| Cetyl alcohol | 17.8 |
| Olive Oil | 7.0 |
| Paraffin oil | 6.0 |

-continued

| Day Creme | |
|---|---|
| Hamamelis extract | 9.0 |
| Preservative | 0.2 |
| (Methyl-4-hydroxybenzoate Na salt) | |
| H$_2$O | 52.0 |
| | 100.0 |

EXAMPLES 9 AND 10

| Eye Make-up Remover | | |
|---|---|---|
| Compound according to Example 2 | 10.0 | 5.0 |
| Compound according to Example 3 | — | 5.0 |
| Polyol fatty acid ester | 5.0 | 5.0 |
| Carbopol 934 (1% solution in water) (Acrylic acid copolymerizate) | 79.8 | 79.8 |
| Preservative (Methyl-4-hydroxybenzoate Na salt) | 0.2 | 0.2 |
| H$_2$O | 5.0 | 5.0 |
| | 100.0 | 100.0 |

EXAMPLE 11

| Oil/water Creme | |
|---|---|
| Compound according to Example 4 | 4.0 |
| Cetyl alcohol | 2.0 |
| Stearic acid | 2.0 |
| Paraffin oil | 2.0 |
| 1,2-propylene glycol | 2.0 |
| Glycerin | 1.5 |
| Preservative (Methyl-4-hydroxybenzoate Na salt) | 0.2 |
| H$_2$O | 85.8 |
| Perfume | 0.5 |
| | 100.0 |

EXAMPLE 12

| Deodorant Lotion | |
|---|---|
| Grillocin HY 7 (Deodorant substance zinc ricinoleate base - Grillo AG) | 2.0 |
| Compound according to Example 1 | 11.0 |
| Isopropyl myristate | 3.0 |
| Carbopol 934 (1% solution in water) (Acrylic acid copolymerizate) | 83.8 |
| Preservative (Methyl-4-hydroxybenzoate Na salt) | 0.2 |
| | 100.0 |

The following example illustrates the solubilizing action of the surfactant produced according to Example 2 for water insoluble substances used in the cosmetic field.

Example 13

| Solubilization | | | | |
|---|---|---|---|---|
| (a) Oil of roses | — | 1 | — | — |
| (b) Bactericide Irgasan DP 300 (Ciba) (2,4,4'-trichloro-2'-hydroxydiphenyl ether) | — | — | — | 1 |
| (c) Deodorant substance Grillocin (Grillo AG) (1) | — | — | 1 | — |
| (d) Menthol | 1 | — | — | — |
| (e) Compound according to Example 2 | 5 | 2 | 4 | 4 |
| (f) H$_2$O | 94 | 97 | 95 | 95 |
| Solubilization | 100.0 | 100.0 | 100.0 | 100.0 |
| | * | ** | ** | ** |

Appraisal:
Clearly soluble = **
Soluble with slight clouding = *
(1) Deodorant substance Zinc ricinoleate base - Grillo AG The substances listed from (a) to (d) are insoluble in water in the absence of the surfactant of the invention.

EXAMPLE 14

| Antiscale Shampoo | |
|---|---|
| Compound according to Example 5 | 10.0 |
| Sodium lauryl ether sulfate (28%) | 50.0 |
| Polyquart H (Polyglycol-polyamine condensation resin - Henkel KGaA) | 5.0 |
| Comperlan KD (Coco fatty acid diethanolamide - Henkel KGaA) | 5.0 |
| H$_2$O | 30.0 |
| | 100.0 |

EXAMPLE 15

| Intimate Care Washing Solution | |
|---|---|
| Compound according to Example 5 | 10.0 |
| Ricinoleic acid monoethanolamide sulfosuccinate | 15.0 |
| Sodium lauryl ether sulfate (28%) | 20.0 |
| Comperlan KD (Coco fatty acid diethanolamide - Henkel KGaA) | 3.0 |
| Polyglycol 400 | 10.0 |
| Polyol fatty acid ester | 7.0 |
| H$_2$O | 35.0 |
| | 100.0 |

EXAMPLE 16

| Footbath | |
|---|---|
| Compound according to Example 6 | 8.0 |
| Sodium lauryl ether sulfate | 30.0 |
| 1,2-propylene glycol | 2.0 |
| H$_2$O | 60.0 |
| | 100.0 |

The good compatibility of the partial esters according to the invention with skin and mucous membranes is evident from the following investigations. In Table 1, the results of an eye irritation test, according to Draize, for the products of the invention are compared with those of anionic surfactants known to be acceptable dermatologically. It should be noted that substantially higher concentrations of the active products of the invention, than of the prior art compounds, were used in the test.

TABLE 1

| Test No. | Product designation | Concentration % active substance | Evaluation points according to Draize score | Evaluation range |
|---|---|---|---|---|
| 1 | Compound according to Example 1 | 100 | 15.6 | Slightly irritant |

TABLE 1-continued

| Test No. | Product designation | Concentration % active substance | Evaluation points according to Draize score | Evaluation range |
|---|---|---|---|---|
| 2 | Compound according to Example 2 | 65 | 1.8 | Non-irritant |
| 3 | Compound according to Example 3 | 100 | 3.6 | Non-irritant |
| 4 | Compound according to Example 4 | 100 | 4.2 | Non-irritant |
| 5 | Compound according to Example 5 | 50 | 6.3 | Non-irritant |
| 6 | Tallow coco fat alcohol sulfate Na salt | 40 | 24.3 | Slightly irritant |
| 7 | Ammonium lauryl sulfate | 35 | 12.9 | Slightly irritant |
| 8 | Na lauryl ether sulfate | 50 | 14.2 | Slightly irritant |
| 9 | Na salt of undecylic acid monethanolamide sulfo succinic acid semi-ester | 50 | 19.6 | Slightly irritant |

The Draize test was performed according to the provisions of the Appraisal of the Safety of Chemicals in Food, Drugs and Cosmetics, published by the United States Food and Drug Administration in 1959. According to this method, appraisal points are assigned as follows:

| Points | Appraisal Ranges |
|---|---|
| 0–10 | non irritant |
| 11–25 | slightly irritant |
| 16–56 | moderately irritant |
| 57–110 | severely irritant |

The bactericidal and fungicidal effectiveness of the partial esters formed using undecylic acid is shown by the data in Table 2 (suspension test using the product of Example 5, concentration 50%).

TABLE 2

| | Test Bacteria | | | |
|---|---|---|---|---|
| | Escherichia coli ATCC11229 | Staphylococcus aureus ATCC5638 | Pseudomonas aeruginosa ATCC15942 | Candida albicans CBS5703 |
| Acting times | Number of test bacteria inoculated for each culture | | | |
| | 1,600,000 | 1,800,000 | 2,500,000 | 770,000 |
| 2.5 minutes | — | — | — | — |
| 5 minutes | — | — | — | — |
| 10 minutes | — | — | — | — |
| 15 minutes | — | — | — | — |
| 1 hour | — | — | — | — |
| Blank value with physiological NaCl solution | ++ | ++ | ++ | ++ |

Explanation of symbols:
— no growth
+ weak growth
++ strong growth

The test was conducted following the guidelines for the testing of chemical disinfectants published by the Deutsche Gesellschaft für Hygiene and Mikrobiologie.

The foregoing detailed description has been given for clearness of understanding only, and no unnecessary limitations should be understood therefrom, as modifications will be obvius to those skilled in the art.

What is claimed is:

1. A product of the group consisting of polyhydric alcohol partial esters of a polycarboxylic acid from a Diels-Alder adduct of maleic anhydride with an unsaturated carboxylic acid having a 10 to 25 carbon chain, and sulfonate derivatives thereof.

2. A product according to claim 1 in which the polyhydric alcohol is a monosaccharide or a disaccharide.

3. A product according to claim 2 in which the unsaturated carboxylic acid has a straight chain.

4. A product according to claim 3 in which the polyhydric alcohol is sucrose, mannose or glucose.

5. A product according to claim 3 in which the unsaturated carboxylic acid is recinoleic acid, oleic acid, linoleic acid, palmitoleic acid, elaidic acid, or undecylenic acid, or a mixture thereof.

6. A cosmetic product suitable for application to the skin containing a partial ester as defined in any one of claims 1 to 5.

7. A dermatologically acceptable cosmetic product in the form of a shampoo, cleansing creme or lotion containing a partial ester as defined in any one of claims 1 to 5 as a surfactant or emulsifier.

8. A product according to claim 1 in which the unsaturated carboxylic acid has a 10 to 18 carbon chain.

9. A product according to claim 1 or 8 in which the unsaturated carboxylic acid is mono-unsaturated.

10. A product according to claim 1 or 8 in which the unsaturated carboxylic acid is mono-unsaturated and the polyhydric alcohol is sucrose, mannose or glucose.

11. A product according to claim 1 in which the unsaturated carboxylic acid is ricinoleic acid, oleic acid or undecylenic acid.

12. A cosmetic product suitable for application to the skin containing a partial ester as defined in any one of claims 8 to 11.

* * * * *